(12) United States Patent
Kantro et al.

(10) Patent No.: US 8,360,987 B2
(45) Date of Patent: Jan. 29, 2013

(54) SYSTEM AND METHOD FOR MONITORING PLANTAR TEMPERATURE OF THE FOOT

(76) Inventors: Scott Kantro, Pound Ridge, NY (US); Andrew M. Singer, South Salem, NY (US); Don Edgerton, Lake Barrington, IL (US)

( * ) Notice: Subject to any disclaimer, the term of this patent is extended or adjusted under 35 U.S.C. 154(b) by 522 days.

(21) Appl. No.: 12/001,493

(22) Filed: Dec. 11, 2007

(65) Prior Publication Data

US 2008/0214962 A1 Sep. 4, 2008

Related U.S. Application Data

(60) Provisional application No. 60/874,285, filed on Dec. 11, 2006.

(51) Int. Cl.
*A61B 5/00* (2006.01)
*A61B 5/103* (2006.01)
*A61B 5/117* (2006.01)

(52) U.S. Cl. .......... 600/549; 600/587; 600/592

(58) Field of Classification Search .......... 600/300, 600/306, 546, 547, 549, 555, 587, 592, 595; 374/16, 17, 18, 19, 29, 30, 137, 141, 142, 374/143, 149, 150, 151, 158, 161, 162, 208, 374/209
See application file for complete search history.

(56) References Cited

U.S. PATENT DOCUMENTS

| | | | |
|---|---|---|---|
| 2,043,187 A | 6/1936 | Owens | 128/2 |
| 3,830,224 A | 8/1974 | Vanzetti et al. | |
| 3,847,139 A | 11/1974 | Flam | |
| 4,148,951 A | 4/1979 | Clar, III | |
| 4,327,742 A | 5/1982 | Meyers et al. | |
| 4,327,743 A | 5/1982 | Katz | |
| 4,379,461 A | 4/1983 | Nilsson et al. | 128/736 |
| 4,534,365 A | 8/1985 | Bonetta et al. | |
| 4,554,930 A | 11/1985 | Kress | 128/774 |
| 4,849,885 A | 7/1989 | Stillwagon et al. | 364/413.1 |
| 5,124,819 A | 6/1992 | Davis | |
| 5,361,133 A | 11/1994 | Brown et al. | |
| 5,642,096 A | 6/1997 | Leyerer et al. | 340/573 |
| 5,678,566 A | 10/1997 | Dribbon | |
| 5,805,245 A | 9/1998 | Davis | 349/20 |
| 6,090,050 A | 7/2000 | Constantinides | 600/549 |
| 6,195,921 B1 | 3/2001 | Truong | 36/136 |
| 6,331,893 B1 | 12/2001 | Brown et al. | 356/601 |
| 6,398,740 B1 | 6/2002 | Lavery et al. | 600/549 |
| 6,708,644 B2 | 3/2004 | McNamara | 116/207 |
| 6,767,330 B2 | 7/2004 | Lavery et al. | 600/549 |
| 6,975,232 B1 | 12/2005 | McKenna | 340/573.1 |
| 2005/0047677 A1* | 3/2005 | Alaimo et al. | 382/286 |

FOREIGN PATENT DOCUMENTS

| | | |
|---|---|---|
| DE | 4416731 | 11/1995 |
| FR | 2607252 | 5/1988 |
| RU | 2214155 | 10/2003 |
| WO | 2004055483 | 7/2004 |

OTHER PUBLICATIONS

Diabetic Foot Information and Resources—Dec. 22, 2006.
European Office Action dated Jun. 23, 2010.
International Search Report dated Dec. 11, 2007.

* cited by examiner

*Primary Examiner* — Jeffrey G Hoekstra
(74) *Attorney, Agent, or Firm* — Sofer & Haroun, LLP

(57) ABSTRACT

A console for measuring plantar foot pressure includes a support case and at least two temperature sensitive pads, disposed in the case, configured to allow a user to measure the temperature of the soles of their feet without assistance.

14 Claims, 2 Drawing Sheets

| |
|---|
| Polycarbonate (3) |
| Tycote ink (4) |
| Chiral Nematic Liquid (5) |
| Cholesteric Liquid Crystal (6) |
| Cholesteric Liquid Crystal (7) |
| Black Leuco dye (8) |
| Florescent Yellow Ink (9) |
| Pressure Sensitive Adhesive (10) |
| 1/8" Closed Cell Foam (11) |

| Polycarbonate (3) |
| :---: |
| Tycote ink (4) |
| Chiral Nematic Liquid (5) |
| Cholesteric Liquid Crystal (6) |
| Cholesteric Liquid Crystal (7) |
| Black Leuco dye (8) |
| Florescent Yellow Ink (9) |
| Pressure Sensitive Adhesive (10) |
| 1/8" Closed Cell Foam (11) |

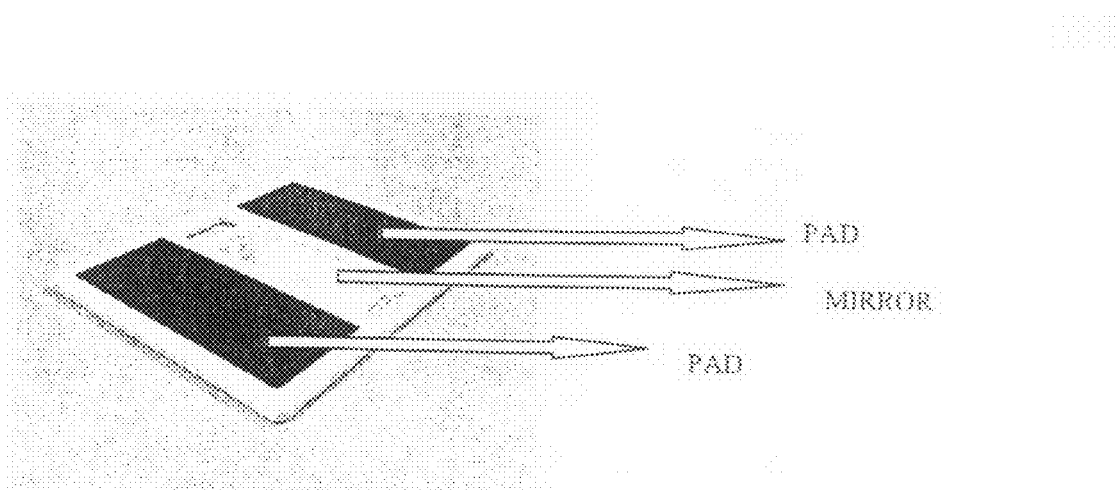
Figure 3: Top view of TempStat unit, identifying each pad and center console mirror.
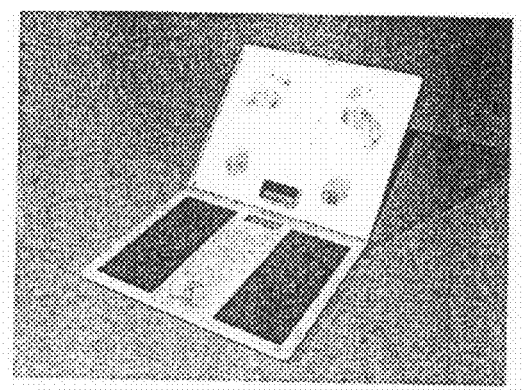
Figure 4: TempStat unit with PressureStat cover

SYSTEM AND METHOD FOR MONITORING PLANTAR TEMPERATURE OF THE FOOT

RELATED APPLICATION

This application claims the benefit of priority from U.S. Provisional Patent Application No. 60/874,285, filed on Dec. 11, 2006, the entirety of which is incorporated by reference.

FIELD OF THE INVENTION

The invention relates to a method and apparatus for facilitating the self-examination of the plantar surface of the foot. It is intended to be used in the home environment, but may be used in clinic as well. Specifically, the invention is intended to assist a person, principally, but not exclusively, a diabetic patient diagnosed with neuropathy, to examine the image and condition of the soles of their feet in connection with a daily self-examination for irritation, abrasions, cuts, bruises, swelling, inflammation and other damage to the sole of the foot that can lead to ulceration.

BACKGROUND OF THE INVENTION

The disease process of diabetes has been studied extensively, and its debilitating effects on its victims and the financial drain on the healthcare system are well documented. The actual disease of diabetes can be controlled with medication, but the side effects and secondary complications of the disease are what cause the real damage to its victims. Foot ulceration is the single most common cause for hospitalization of diabetic patients. Foot ulceration occurs as a result several factors, but the most important cause is the lack of patient awareness of the potential problem and their subsequent lack of attention and care of the cause of the foot ulcers. Peripheral neuropathy plays a role in diminishing the feeling in the patient's foot, and incorrectly providing the patient with a sense of well-being through a lack of any pain or sensation.

Ulceration on the sole of the foot is most often preceded by an increase in skin surface temperature at the pre-ulceration and ulceration site. The ADA, as well as other clinical practice guidelines, suggests that diabetic patients with neuropathy should monitor their feet for temperature changes that could indicate that inflammation is present and an ulcer could develop. However, just informing a patient that due to their neuropathy they are at higher risk for foot ulceration, without providing them a simple means to monitor the temperature and condition of the soles of their feet (which they likely can't see or even touch) is not effective.

As described in U.S. Pat. No. 5,678,566 to Dribbon, thermography has been identified as a potential diagnostic tool is in the treatment of the diabetic and insensate foot patient. Unable to feel pain, the insensate foot patient is at great risk of foreign body infiltration, shoe irritation and the trauma caused by simple ambulation. It has been found that typically only after blood appears on the sock or shoes will such a patient seek treatment, but by that time serious damage may have already occurred. Research has been conducted with respect to the effectiveness of contact thermography as a diagnostic tool to detect areas of tissue damage and inflammation which can lead to ulceration on the plantar surface of the foot. See Stess et al.: "Use of Liquid Crystal Thermography in the Evaluation of the Diabetic Foot," Diabetes Care., 9(3):267-272 (May-June, 1986); Benbow et al.: "The Prediction of Diabetic Neuropathic Plantar Foot Ulceration by Liquid-Crystal Contact Thermography," Diabetes Care, 17(8) 835-639 (August, 1994); and Dribbon: "Thermography and Diagnosis," Pain Practitioner, the Quarterly Newsletter, pp. 3-4. As explained in these articles, tests indicate that contact thermography is a viable diagnostic tool which is capable of providing an indication of abnormalities in the diabetic foot even before the occurrence of ulceration or other tissue damage.

There have been a number of prior patents filed to measure visual pattern of infrared heat emissions from a particular area of the body employing thermochromic liquid crystal technology (See U.S. Pat. No. 5,124,819, Davis, U.S. Pat. No. 5,678,566, Dribbon, U.S. Pat. No. 4,327,742, Meyers et. al., U.S. Pat. No. 4,327,743, Katz).

Unfortunately, the mechanisms and devices used in each of these prior uses of LCT and the devices themselves were not tailored specifically to enable a diabetic patient to use the device in the home environment on a daily basis to monitor and examine the planter surface of the foot. Specifically, these prior uses failed to optimize the device so that (i) temperature differences represented by color changes would be readily apparent to the home user and not require the skill of a physician to interpret results and (ii) the design of the device itself would facilitate its use as a tool for contra-lateral comparison and visual self-examination in the home environment.

A detailed discussion of LCT can be found in the publication "The Hallcrest Handbook of Thermochromic Liquid Crystal Technology" published by Hallcrest Products, Inc. of Glenview, Ill., the disclosure of which is hereby incorporated by reference in its entirety herein.

OBJECTS AND SUMMARY

The subject invention is a simple, easy to use, low-cost, device that enables a patient to compare his or her left and right thermal foot images for noticeable differences in temperature at specific areas on the sole of the foot that may indicate that inflammation is present and ulceration may soon follow. The subject invention accurately measures plantar temperature variations using liquid crystal thermal-imaging technology ("LCT"), coupled with single temperature range leuco dye. The subject invention incorporates a proprietary layering system of multiple layers of LCT to stimulate color changes at the level relevant to the monitoring of temperature changes in a foot that may be in the early or late stages of inflammation. The subject invention also incorporates a magnification mirror to facilitate visual self-examination, both in connection with an adverse temperature reading as well as independently.

For purposes of the present discussion, thermochromic liquid crystals are heat-sensitive and have the property of exhibiting different colors, when visualized against a black background, indicative of the temperature of an object placed thereagainst. As described below in connection with a discussion of method of diagnosis of this invention, the LCT's are useful in providing an indication of the infrared thermal emissions from the plantar surface of the foot of a particular patient.

The subject invention significantly improves the ability to differentiate temperature differences by combining LCT technologies and setting specific temperature ranges so differences in the higher temperature ranges will be more noticeable. Further, the subject invention has incorporated an additional single temperature event marker, with a distinctive color separate from the colors in the LCT spectrum, which is triggered at a preset temperature to alert a patient that an area has approached the highest temperature range. To overcome ease of use issues by patients with limited mobility, the invention was designed to be used from a seated position to provide the patient with a clear comparative reference view. Additionally, the subject invention was designed to incorporate a magnification mirror to facilitate visual self-examination, both in connection with an adverse temperature reading as well as independently. Finally, in various forms of the invention, the design includes the incorporation of a plantar pressure map to assist the patient to focus on high risk areas of the plantar surface of the foot.

It is a first object of the present invention to use a temperature measuring device to identify higher (or lower) temperature areas of the plantar surface of the foot.

It is another object of the present invention to provide a device not to identify specific plantar temperatures (i.e. by providing specific temperature outputs in numerical degrees), but to operate by creating an easy to understand visual-based comparison between the feet.

It is another object of the present invention to provide a device to create an easily identifiable visual difference between contra-lateral feet when one foot has an area of higher (or lower) temperature that is not present on the other foot. Achieved by placing mats side-by-side.

It is another object of the present invention to provide a device to be able to used by patients, including diabetic patients that may be suffering from obesity or otherwise have limited mobility or the ability to examine the plantar surface of their feet. Achieved by ability to use from a seated or standing position with no requirement to reach, touch or see the plantar surface of the foot.

It is another object of the present invention to provide a device to have a magnification mirror incorporated within the device to allow visual self-inspection of the plantar surface of the foot apart from or in connection with temperature monitoring.

It is another object of the present invention to provide a specific number of layers of LCT required to create the intended visual effect of identifying high (or low) plantar temperatures in a comparative visual representation.

It is another object of the present invention to provide specific temperature ranges of the LCT layers which are relevant identifying both normal and abnormal temperature conditions on the plantar surface of the human foot.

It is another object of the present invention to provide specific temperature ranges of the LCT layers specific to identify higher temperature areas (e.g. caused by inflammation and infection) or lower temperature areas (e.g. caused by PVD) on the plantar surface of the human foot.

It is another object of the present invention to provide specific temperature ranges of the LCT layers to create a footprint even below normal temperature ranges to enable a patient to see a footprint even in a colder environment, where no LCT reaction would normally occur.

It is another object of the present invention to provide specific temperature ranges of the LCT layers to create a visible differentiation between a higher (or lower) temperature area on the subject foot and the normal contra-lateral foot.

It is another object of the present invention to highlight the differentiation between a higher temperature area on the subject and the normal contra-lateral foot by introducing a leuco dye or other similar temperature sensitive compound (the "Highlight Indicator") that reacts with one specified distinctive color at one specific temperature setting.

It is another object of the present invention to incorporate the Highlight Indicator in a specific layer of the LCT mat to maximize its effect.

It is another object of the present invention to incorporate a plantar pressure assessment footprint (e.g. PressureStat) to provide increased awareness of high plantar pressure as a risk factor in developing ulceration.

It is another object of the present invention to incorporate a plantar pressure assessment footprint (e.g. PressureStat) to provide the patient with a visual "map" of their high plantar pressure areas so they can focus their attention on those specific areas while using the device.

It is another object of the present invention to incorporate a plantar pressure assessment footprint (e.g. PressureStat) within the design of the device to provide a visual reference that can be easily seen while using the device. In one version of the device, the PressureStat would be inserted into the inside front cover of the device (which opens to 135°) in specifically designed recessed holders. In another version of the device, the PressureStat would be inserted into specifically designed sleeves on the laminated instruction card.

BRIEF DESCRIPTION OF THE SEVERAL VIEWS OF THE DRAWING

FIG. 3 is a top view of the console, with pads as show in FIG. 1, in one accordance with one embodiment of the present invention; and FIG. 4 is a top view of the console, with pads as show in FIG. 1, having an additional pressure sensor pad, in one accordance with one embodiment of the present invention.

DETAILED DESCRIPTION

Figures 1, 2:
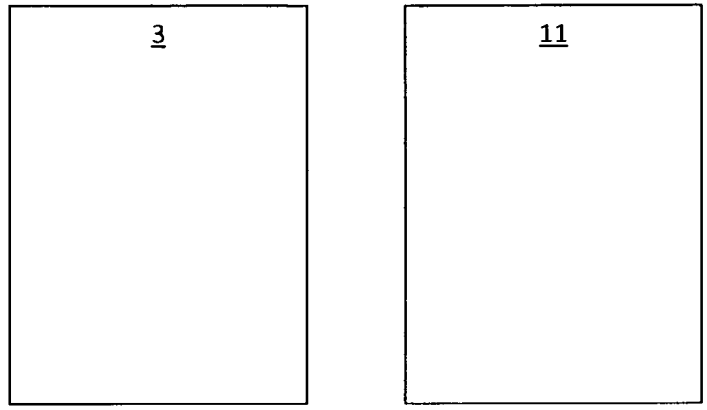
FIG. 1 is a top view of an LCT pad in accordance with one embodiment of the present invention.
FIG. 2 is a side view of the pad of FIG. 1, showing the various layers, in one accordance with one embodiment of the present invention.

In the preferred embodiment of the invention, the pads (FIG. 1) were designed as 6"×14" rectangles to be of a size that would accommodate most foot sizes with sufficient viewing area for the imprint. In the preferred embodiment of the invention, a matte, 7 mil Polycarbonate Film 3 was placed on the surface to protect the LCT layers, enable superior viewing and photography of the thermal image without glare and to make it easy to clean, but any similar protective layer would be sufficient. In the preferred embodiment of the invention, a ⅛" Closed Cell Foam backing 11 was affixed to provide insulation for the LCT as well as a soft, non-slip surface, but any similar backing would be sufficient.

FIG. 2 shows the preferred embodiment of the invention, with A 7 mil polycarbonate film (3) with a Tycote ink layer (4), a chiral nematic liquid crystal layer (5), two cholesteric liquid crystal layers (6), (7), a leuco dye layer (8), a florescent yellow ink (9), Pressure sensitive adhesive (10) and backed with ⅛" closed cell foam (11).

The temperature events are represented by one formulation of chiral Nematic liquid crystals, two formulations of cholesteric liquid crystals and one leuco dye formulations applied to the back of the polycarbonate film which change color in sequence as defined in ASTM specification E1061 for Direct Reading Liquid Crystal Forehead Thermometers.

The formulation of the layers of the pads were chosen to obtain the desired specificity of image at the various temperature ranges. In the preferred embodiment of the invention, the temperatures of the layers were calibrated approximately as follows:

TABLE 1

| Layer | Liquid Crystal Start of Red Specification (° F.) | Liquid Crystal Start of Green Specification (° F.) | Liquid Crystal Start of Blue Specification (° F.) | Leuco Dye Color to Clear on Heating Specification (° F.) |
|---|---|---|---|---|
| 1 | 60.0 | n/a | 70.0 | n/a |
| 2 | 74.0 | 75.0 | 80.0 | n/a |
| 3 | 82.0 | 83.0 | 86.0 | n/a |
| 4 | n/a | n/a | n/a | 87.8 |

The first layer is composed of a Chiral Nematic Liquid Crystal due to its expanded temperature range and clearer color imaging. The purpose of the first expanded range was to always obtain a clear, thermal image even in lower temperature environment (approximately 60-70 degrees F.). It was thought that failure to achieve a thermal image at all times would frustrate the patient and cause him or her to cease using the invention. A Chiral Nematic layer was used for superior imaging at a broader range. A 2 degree temperature spread per color change was deemed to be sufficient for readings at this temperature range.

The second layer was set to achieve a clear thermal image in the mid-range (approximately 74-80 degrees F.). The purpose of the second layer was again to provide a clear thermal image, but as the this mid-range was closer to the norm for a healthy foot, the tolerance between color change events was lowered to approximately 1.5 degrees to enable a clearer differentiation at closer relative temperatures. By compressing the range to a 6 degree spread, this clearer color differentiation between smaller temperature intervals is achieved.

The third layer was constructed specifically to identify temperature changes in the neuropathic foot, which has a higher mean foot temperature than a healthy foot. In this layer, the temperature spread was compressed to a four degree F. spread, so that an identifiable color change would in tighter temperature intervals—closer to 1 degree F. intervals. As the average foot temperature was determined to be 82 degrees, we designed this layer to achieve a glow-green color at this normal range so that higher temperature areas (represented by increasingly darker blue colors) would be readily apparent and clearly distinguishable. The purpose of the tighter spread is to enable a more clearly discernible and differentiated color pattern at the higher end of the range so that temperature differentials at the higher end of the range were readily apparent.

Finally, the fourth layer consists of a leuco dye was set to clear (and reveal the florescent yellow ink backing) at approximately 88 degrees, because high risk temperature for inflammation is scientifically proven to be between 88 and 90 degrees F. The purpose of the leuco dye is to reveal a clearly distinctive florescent yellow ink at the highest end of the range so that a very distinctive color differentiation from the contra-lateral footprint is observed.

The thermal image of the patient's feet will normally take 10-30+/−5 seconds to fully develop and is dependent upon contact not pressure. Once the patient removes their feet from the temperature sensing surface, the thermo-graphic map will degrade back to the original appearance at room temperature within minutes. However, the areas indicative of the hottest foot contact temperatures ("Hot Spots") will be clearly discernable compared to adjacent areas of the thermal image of that foot and the same position on the thermal image of the contra-lateral foot. Further, the hottest areas will be the last to degrade and there will be ample time (as much as one minute or more) for the patient or a care giver to note this difference.

The Leuco indicator is designed to last even longer than the LCT so that the fluorescent yellow spot which appears at the highest temperature range will last the longest. It is also very easy to take digital photos. The matt surface of the mat's Lexon surface prevents reflections that would impair photo quality.

Part of the problem with simply using multiple LCT layers to create differentiation is that it is sometimes it is difficult to visually identify differences between color patterns since sometimes a higher temperature will be indicated by a color at the highest end of the subject range (e.g. violet "hot spot" on green background), but in other times, if the temperature has risen to a range in the beginning of the second LCT layer and is in the lower end of that color spectrum (e.g. green), the higher temperature would be represented by a lighter color (e.g. green "hot spot" on violet background).

The subject invention overcomes these obstacles in the preferred embodiment by specifically setting the ranges of the three LCT layers to identify focal increases in plantar temperature specifically targeted to the neuropathic foot and therefore making visual identification of relevant color differences between contra-lateral thermal images easier to identify. Under normal circumstances, the base temperature of a neuropathic foot is between 82 and 85 degrees F. In the preferred embodiment of the invention, the temperature ranges of the pads were specifically so that:

1. A clear thermal footprint would be observable even at lower temperatures to account for "cold" feet (e.g. after walking over a cold floor) and provide a background image of footprint so that if inflammation was present on a "cold" foot, the "hot spot" would be identifiable within the confines of a footprint. Otherwise, a "hot spot" might have registered, but would not be identifiable to a specific area of the foot since no frame of reference would have been provided. The importance of this layer also relates to its ability to always form a print and therefore not discourage patients from using the device if a footprint, even on "cold" feet were not observable.

2. A clear thermal footprint would continue to appear through the temperature range most common for a "normal" foot. The second layer was primarily constructed to provide a bridge from the upper range of the first layer to the beginning of the third layer.

3. At the average mean temperature for the neuropathic foot (between 82 and 85 degrees F.), the thermal image of the footprints would glow green to provide a compelling background for the higher temperature range color spectrum (blue to violet to florescent yellow). This range was designed with a 4 degree spread so that it would be more reactive to smaller incremental temperature changes and therefore change color to identify "hot spots" approximately every 1 degree F. so that temperature differences would be more noticeable.

4. At the average mean temperature for inflammation (88 to 90+ degrees F.) a fourth layer, consisting of a leuco dye, would clear and identify this highest and most dangerous temperature level. In the preferred embodiment of the invention, a leuco dye was chosen due to its ability to clear at a specific temperature range (within a 2 degree F. tolerance) and reveal a distinctive color or color pattern. As described earlier, since it is sometimes difficult to determine a "hot spot" based on a specific color change in the LCT spectrum due to overlapping multi-eventing, a leuco dye was chosen so that a distinct color (florescent yellow) would emerge as a "hot spot" that could not be confused with an earlier LCT event color and could be easily identified by a patient using the device to connote danger. Therefore, by incorporating a florescent yellow, a color that is distinctive and not present in any LCT color pattern, the patient is alerted to a dangerously high focal temperature "hot spot" in a clearly distinctive fashion.

The device itself was designed to promote ease of use—a patient simply places his or her feet on the temperature sensitive pads for 60 seconds from a comfortable sitting position.

The preferred embodiment of the proposed invention (FIG. 3) is ergonomically designed to be used by patients with obesity and limited joint mobility that would otherwise not be able to reach or even see the bottoms of their feet. The frame will be light weight yet strong enough for any patient to stand on. The preferred embodiment of the frame is as depicted in FIG. 3, but could be any flat or folding surface where the pads and mirror could be affixed. In an alternate form of the invention, the mirror could be placed on the opposite side rather that the center console for viewing.

There are two thermographic sensing surfaces on the top surface of the frame, one for each foot, each measuring 6" wide×14" length. The 20" width of the screening surface will enable patients place their feet on the pads in a comfortable stance. The device is placed on the floor. The patient simply places one foot on each of the pads from a seated or standing position sufficient to maintain contact for 60 seconds (60 seconds is ideal, but a shorter duration is sufficient as well). The feet are removed from the pads and the thermographic images are observed. If significant color differences both feet on the mat so the full plantar surfaces are in contact. Since the thermal sensing capability of the mat is not influenced by pressure (beyond that required to create full contact), the patient can do this from either a standing or a seated position as long as the full plantar surfaces are in full contact with the mat. The patient's feet can either be bare or they can be wearing thin socks or stockings. After approximately 6tgv0 seconds of contact, the feet are removed from the mat and a full field thermal image will be presented of the plantar surfaces of both feet. Once appropriately instructed, patients (or a caregiver) will be able to assess their feet for "hot spots" and alter their activity.

The proposed invention was designed specifically to enhance the ability to use contra-lateral comparison to evaluate "hot spots". By placing the pads side by side in the frame, it is easy to visually compare the left thermal image to the right thermal image for noticeable differences.

The proposed invention was also designed specifically to facilitate self-examination by incorporating a 2× magnification mirror. The purpose of the mirror is to allow a patient to easily examine the sole of the foot—an area of the body inaccessible for viewing by an overweight or inflexible patient—either as part of the daily temperature examination or separately. Simply creating another mechanism to facilitate and encourage a self-examination by a patient of his or her feet is very beneficial to the diabetic population. As part of the proposed invention, the mirror allows a patient to immediately examine those areas of the foot that are represented by higher temperatures on the LCT pads and better communicate any problems to their healthcare provider. For those home users who do not have the benefit of a friend, family member or healthcare provider to examine their feet for signs of irritation, abrasions, cuts, bruises, swelling, inflammation and other damage to the sole of the foot that can lead to ulceration, the incorporated mirror provides a means to do so. In the preferred embodiment of the invention, the mirror is placed in the center console for easy viewing of the plantar surface of the foot after the foot has been removed from the pads. However, the incorporated mirror could be placed in other areas in other embodiments of the invention.

Another purpose of this invention is to combine plantar temperature detection with plantar pressure detection. In order to more specifically focus a patient's attention on the most high risk areas of the foot, it is the purposes of this invention to integrate a patient's plantar pressure assessment within the invention. As ulcerations are more likely to occur in the high plantar pressure areas, the benefits of providing a patient with this plantar pressure "map" are significant. To this end, in one embodiment of the invention, a patient's plantar pressure assessment, on a PressureStat™ or similar device, would be placed in easy view of the patient while utilizing the invention. In one version, the device itself would include a plastic cover with a recessed area specifically designed to accept a PressureStat. In another more portable version of the invention, there would be no cover, but a large laminated instruction card or similar device would accompany the device with specific sleeves intended to hold the PressureStat prints and be easily viewed by the patient while using the invention.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A console for measuring plantar foot temperature, said console comprising:
    a support case; and
    at least one temperature sensitive pad, disposed in said case, configured to allow a user to measure the temperature of a sole of one of their feet without assistance,
    wherein said temperature sensitive pad has at least first, second and third layers, which together form an overall plantar foot temperature profile for said user's foot
    wherein said first layer is configured to produce a first color response in a first temperature range, said second layer is configured to produce a second color response in a second temperature range and said third layer is configured to produce a third color response in a third temperature range, such that said color responses of first second and third layers are together calibrated to produce a thermal image within defined temperature ranges that is targeted to identify focal increases in plantar temperature so as to allow visual identification of areas of inflammation in a neuropathic foot.

2. The console as claimed in claim 1, further comprising two temperature sensitive pads allowing the user to compare the temperature of the soles of their feet to one another.

3. The console as claimed in claim 1, wherein said first layer is a chiral nematic liquid crystal layer configured to obtain a clear thermal image in the range of substantially 60-70 degrees F.

4. The console as claimed in claim 1, wherein said second layer is a cholesteric layer configured to obtain a clear thermal image in the range of substantially 74-80 degrees F.

5. The console as claimed in claim 1, wherein said third layer is a cholesteric layer configured to obtain a clear thermal image in the range of substantially 82 degrees F.

6. The console as claimed in claim 1, further comprising a fourth layer that is a leuco dye layer configured to obtain a clear thermal image in the range of substantially 88 degrees F, with a distinctive color differentiation from the thermal image of said first, second and third layers.

7. The console as claimed in claim 3, wherein said temperature sensitive pad further comprises a tycote ink layer disposed over said first chiral nematic liquid crystal layer.

8. The console as claimed in claim 6, wherein said temperature sensitive pad further comprises a florescent yellow ink layer disposed under said leuco dye layer.

9. The console as claimed in claim 1, wherein said temperature sensitive pad further comprises a polycarbonate film as a top layer to reduce glare.

10. The console as claimed in claim 1, wherein said temperature sensitive pad further comprises a pressure sensitive adhesive and closed cell foam as a bottom layer.

11. The console as claimed in claim 1, wherein said first, second, third and fourth layers change color in sequence as defined in ASTM specification E1061 for Direct Reading Liquid Crystal Forehead Thermometers.

12. The console as claimed in claim 1, wherein said temperature sensitive pad is configured to develop fully within substantially 5-35 seconds.

13. The console as claimed in claim 1, further comprising a mirror to assist a user in viewing the areas of their foot that appear to be negatively affected as per the results of the at least one temperature sensitive pads.

14. The console as claimed in claim 1, wherein said console further comprises an area for receiving a plantar foot pressure measurement for comparison against said at least one temperature sensitive pads.

* * * * *